(12) United States Patent
Chang et al.

(10) Patent No.: US 6,835,568 B2
(45) Date of Patent: Dec. 28, 2004

(54) REGULATED NUCLEIC ACID EXPRESSION SYSTEM

(75) Inventors: Yung-Nien Chang, Cockeysville, MD (US); Yajin Ni, Gaithersburg, MD (US); Boro Dropulic, Ellicott City, MD (US)

(73) Assignee: Virxsys Corporation, Gaithersburg, MD (US)

( * ) Notice: Subject to any disclaimer, the term of this patent is extended or adjusted under 35 U.S.C. 154(b) by 5 days.

(21) Appl. No.: 10/020,472

(22) Filed: Oct. 30, 2001

(65) Prior Publication Data

US 2003/0087419 A1 May 8, 2003

(51) Int. Cl.[7] .............................................. C12N 15/00
(52) U.S. Cl. ..................... 435/440; 435/69.1; 435/70.1; 435/320.1; 435/455; 435/476; 536/23.4; 536/23.72
(58) Field of Search ............................... 435/69.1, 91.1, 435/91.2, 320.1, 455, 456, 457, 70.1, 465, 440, 476; 536/23.4, 23.72

(56) References Cited

U.S. PATENT DOCUMENTS

| | | | |
|---|---|---|---|
| 5,750,396 A | 5/1998 | Yang et al. | 435/357 |
| 5,885,806 A | 3/1999 | Dropilic et al. | 435/91.41 |
| 5,965,726 A | 10/1999 | Pavlakis et al. | 536/23.72 |
| 5,972,596 A | 10/1999 | Pavlakis et al. | 435/5 |
| 6,168,953 B1 | 1/2001 | Dropulic et al. | 435/455 |
| 6,174,666 B1 | 1/2001 | Pavlakis et al. | 435/5 |
| 6,410,257 B1 | 6/2002 | Dropulic et al. | 435/29 |

FOREIGN PATENT DOCUMENTS

| | | |
|---|---|---|
| EP | 0449116 A1 | 3/1991 |
| EP | 0449116 B1 | 8/1999 |
| WO | WO 00/65076 | 11/2000 |

OTHER PUBLICATIONS

Ghosh et al Synergism between Tat and VP16 in Trans–activation of HIV–1 LTR. Journal of Molecular Biology (1993) Vo. 234, pp. 610–619.*

Gossen et al. "Tight control of gene expression in mammalian cells by tetracycline–responsive promoters" Proc. Natl. Acad. Sci., USA 89:5547–5551 (1992).

Adachi et al. "Production of Acquired Immunodeficiency Syndrome–Associated Retrovirus in Human and Nonhuman Cells Transfected with an Infectious Molecular Clone" Journal of Virology 59(2):284–291 (1986).

Chang et al. "Regulation by HIV Rev Depends Upon Recognition of Splice Sites" Cell 59:789–795 (1989).

Chang et al. "The Basic RNA–Binding Domain of HIV–2 Tat Contributes to Preferential Trans–Activation of a TAR2–Containing LTR" Nucleic Acids Research 20(20):5465–5472 (1992).

Hammarskjold et al. "Human Immunodeficiency Virus *env* Expression Becomes Rev–Independent If the *env* Region Is Not Defined as an Intron" Journal of Virology 68(2):951–958 (1994).

Katri et al. "A Packaging Cell Line for Lentivirus Vectors" Journal of Virology 73(1):576–584 (1999).

Klages et al. A Stable System for the High–Titer Production of Multiply Attenuated Lentiviral.

Yu et al. "Inducible Human Immunodeficiency Virus Type 1 Packaging Cell Lines" Journal of Virology 70(7):4530–4537 (1996).

International Search Report, mailed on Oct. 27, 2003, for PCT patent application No. PCT/US02/34932, filed on Oct. 30, 2002, 4 pages.

* cited by examiner

*Primary Examiner*—Ulrike Winkler
(74) *Attorney, Agent, or Firm*—Morrison & Foerster LLP

(57) ABSTRACT

The present invention provides nucleic acid constructs, expression systems, and methods relating to the regulation of gene expression. The invention may be applied to regulate the expression of any coding sequence of interest, including those coding for viral components necessary for the packaging of viral particles.

19 Claims, 6 Drawing Sheets

US 6,835,568 B2

REGULATED NUCLEIC ACID EXPRESSION SYSTEM

TECHNICAL FIELD OF THE INVENTION

The present invention relates to a system for the regulation of gene expression. The invention provides improved nucleic acid constructs capable of tightly regulating the expression of a coding sequence of interest. Tight regulatory control is desirable where the nucleic acid to be expressed, or the level of expression, is toxic to the cellular or host environment in which expression occurs. The invention also relates to the application of the expression system in cells used to package viral vectors and provides methods of preparing the necessary nucleic acid constructs as well as their use in the control of recombinant viral gene expression. In one aspect, the invention relates to the regulation of gene expression in a stably transfected cell.

BACKGROUND OF THE INVENTION

Recombinant nucleic acid technology has proven to be a powerful tool for the expression of the products encoded by nucleic acids of interest. This has resulted in the ability to produce polypeptides and nucleic acids for both research and commercial applications.

Some encoded products, however, are toxic to the cellular or host environment in which their expression occurs, either because the product is inherently toxic or because the levels at which expression occurs is so high as to result in toxicity. One means of dealing with this difficulty has been to use transient expression systems wherein the encoded product is expressed and recovered before toxicity results in reduced levels of product. Alternatively, the encoded product is placed under a tightly controlled regulation system such that the product may be expressed and then expression terminated before toxicity rises to lethal levels. One example of a tightly controlled regulatory system is seen with the use of a tetracycline regulated operator/promoter in combination with a tet repressor (see for example U.S. Pat. No. 5,750,396).

The expression of a toxic product is of particular importance in situations where the product must be continually expressed because it is a component of a larger product being produced, or metabolic activity being conducted, by the cell. One example of such a situation is in the case of a viral packaging cell line, which expresses products necessary for the assembly and packaging of viral particles. If any one of the necessary viral gene products is toxic to the cell, the need to control its expression becomes critical if a stable (as opposed to transient) packaging cell line is to be used. One example of a necessary toxic viral gene is in the case of the G protein from vesicular stomatitis virus (VSV), which is desirable for the production of pseudotyped viral particles.

An example using the tet operator and repressor to regulate the expression of VSV-G is described by Henriette et al. (J. Virol. 73(1):576–584, 1999), where the tet repressor (as a chimeric fusion product with a domain of VP-16 and referred to as tTA) is under the control of a cytomegalovirus (CMV) promoter and VSV-G is under the control of a tet operator. Expression of the chimeric repressor in the absence of tetracycline results in no expression of VSV-G. The presence of tetracycline prevents association between tTA and the tet responsive elements (TRE) found in the operator to allow the expression of VSV-G. This system is referred to as "tet-on" where the presence of tetracycline results in the expression of the gene of interest (i.e. VSV-G).

There is also an alternative "tet-off" system where tTA is a chimeric transactivator. It cannot bind to the TRE of a tet operator in the presence of tetracycline. But in the absence of tetracycline, tTA binds to the operator and strongly activates the promoter to express a coding sequence of interest.

Klages et al. (Molec. Therap. 2(2):170, 2000) teach the use of a similar two nucleic acid system to control VSV-G expression. The first nucleic acid expresses tTA which then controls a TRE containing tet operator that controls VSV-G expression. The same tTA protein also regulates expression of the rev protein which in turn regulates the expression of the gag and pol regions (necessary for viral packaging) by controlling the splicing of the gag/pol messenger RNA via a rev responsive element (RRE).

Another example of the use of the rev protein to control gene expression was described by Yu et al. (J. Virol. 70(7):4530–4537, 1996). They used the expression of tTA to regulate the expression of both HIV-1 rev and envelope proteins which were simultaneously under the regulation of a single TRE containing tet operator. The rev protein then in turn regulates expression of the viral envelope protein, via an RRE, as well as the expression of the gag/pol messenger RNA via another RRE. While transcription of the gag/pol coding sequences was regulated by another promoter, its expression was directly regulated by the rev protein and thus indirectly regulated by tTA.

BRIEF SUMMARY OF THE INVENTION

The present invention provides nucleic acid (expression) constructs and methods for regulating the expression of one or more than one coding sequence of interest. The nucleic acid constructs are preferably recombinant in nature and include at least three constructs where the last one contains the coding sequence of interest. The constructs may be viewed and used as an expression system to express the coding sequence of interest, where each construct express a product that regulates the expression of the next construct in turn so that ultimately, expression of the coding sequence of interest via the last construct is controlled. Each construct preferably, and individually, contains a regulatory region, such as a promoter (optionally with an operator).

In one aspect of the invention, the expression system is utilized as part of a cell or cell line, used to package viral vectors, to regulate expression of components needed to package the vector. The expression system may be used to regulate expression of viral structural or regulatory gene products necessary for packaging a viral vector of interest. Where more than one viral gene product of interest is to be expressed, they may be located on separate nucleic acid molecules and still remain part of the expression system of the present invention. The expression systems of the invention may thus have constructs in common such that two or more systems may be combined to express two or more coding sequences of interest regulated by said systems. Examples of systems with constructs in common include the use of the same first and second nucleic acid constructs but with two third constructs containing two coding sequences of interest, both of which are regulated by the same mechanism via the first and second nucleic acid constructs.

In another aspect of the invention, expression from the first nucleic acid construct is preferably tightly regulated or even autoregulated. One non-limiting example is through a positive feedback mechanism where the product of the first nucleic acid construct can repress its own expression. In the absence of activation, this autoregulation of the first nucleic acid construct allows for a very low basal activity such that little to no expression of the coding sequences of interest (in a additional nucleic acid construct) occurs. Once expression of the first nucleic acid construct is activated, the expression of all additional constructs in the system follows. Autoregulation of the first construct is used in preferred embodiments of the invention to maximize control of expression from the additional constructs in the system.

The constructs and systems of the invention may be incorporated into vectors or introduced into cells. With cells, the constructs may be integrated into the cellular genome or maintained as episomal constructs. The choice of cell is not critical so long as it is permissive for the expression of the constructs and systems of the invention. In embodiments of the invention wherein the cells are used to package viral vectors, the resultant viral vector is preferably complement resistant.

Each construct of the invention may be present on an individual nucleic acid molecule or present on the same nucleic acid molecule as one or more than one of the other constructs (for example, but not limited to, the same plasmid, vector, or chromosome). In preferred embodiments of the invention where the expression system is used in cells to package viral vectors, the individual constructs are preferably divided into separate nucleic acid molecules. The presence of the constructs on one or more than one nucleic acid molecule is generally not critical to the practice of the invention so long as the arrangement of constructs does not result in interference of each construct's ability to regulate the expression of any subsequent construct.

Alternatively, and in an additional aspect of the invention, the constructs are positioned such that there is a regulatory effect arising from the arrangement. A non-limiting example is where two constructs are positioned on one molecule so that their promoters are oriented to express sequences divergently (where the 5' portions of each promoter are closer together than the 3' portions of each promoter) so that activation of one promoter increases the ease of activating the other. This arrangement on plasmids, when used in cells to package viral vectors, has been found to increase the titer of vector production. The arrangement may be mirrored in cells containing a stable integration of nucleic acid constructs by preparing two constructs to be divergently oriented on a single molecule and then integrating the molecule into cellular genome. The divergent orientation would thus be maintained along with the relative positions of the two constructs.

In a further aspect of the invention, one or more than one product expressed by one or more than one construct of the invention is preferably viral in origin and capable of stringently controlling expression from another construct. A preferred expression system of the invention thus expresses one or more than one viral regulatory protein which can regulate expression from another construct of the system.

The constructs and systems of the invention are preferably used to regulate the expression of sequences coding for a product or products toxic to a cell or host, such as, but not limited to, viral proteins. The constructs and systems may also, of course, be used to regulate the expression of non-toxic products.

In one preferred aspect of the invention, the constructs of the invention are incorporated into cells used to package viral vectors into viral particles. Such cells may be referred to as "packaging cells" because they produce all the necessary components to package viral vector nucleic acids into viral particles. Recombinant viral nucleic acids, optionally containing other heterologous or endogenous sequences of interest, may be packaged by such cells. In aspects of the invention where the nucleic acid constructs result in an inducible system to regulate expression of the necessary viral components, such cells may also be viewed and used as an inducible system for packaging viral particles.

The constructs of the invention may be introduced into cells to result in the maintenance of the constructs as extrachromosomal and/or integrated copies. In preferred embodiments of the invention, integration of the constructs is used to produce a stably transfected cell line that may be used to package viral particles for an extended or indefinite period of time.

The invention also provides methods for the production of the constructs and systems described above as well as methods for the use of such systems to regulate expression of coding sequences. These methods include the use of the invention to produce one or more than one component necessary for packaging a viral vector. Kits containing the constructs of the invention or for use with the disclosed methods are also provided.

DESCRIPTION OF THE PREFERRED EMBODIMENTS

Definitions

Figure 1:
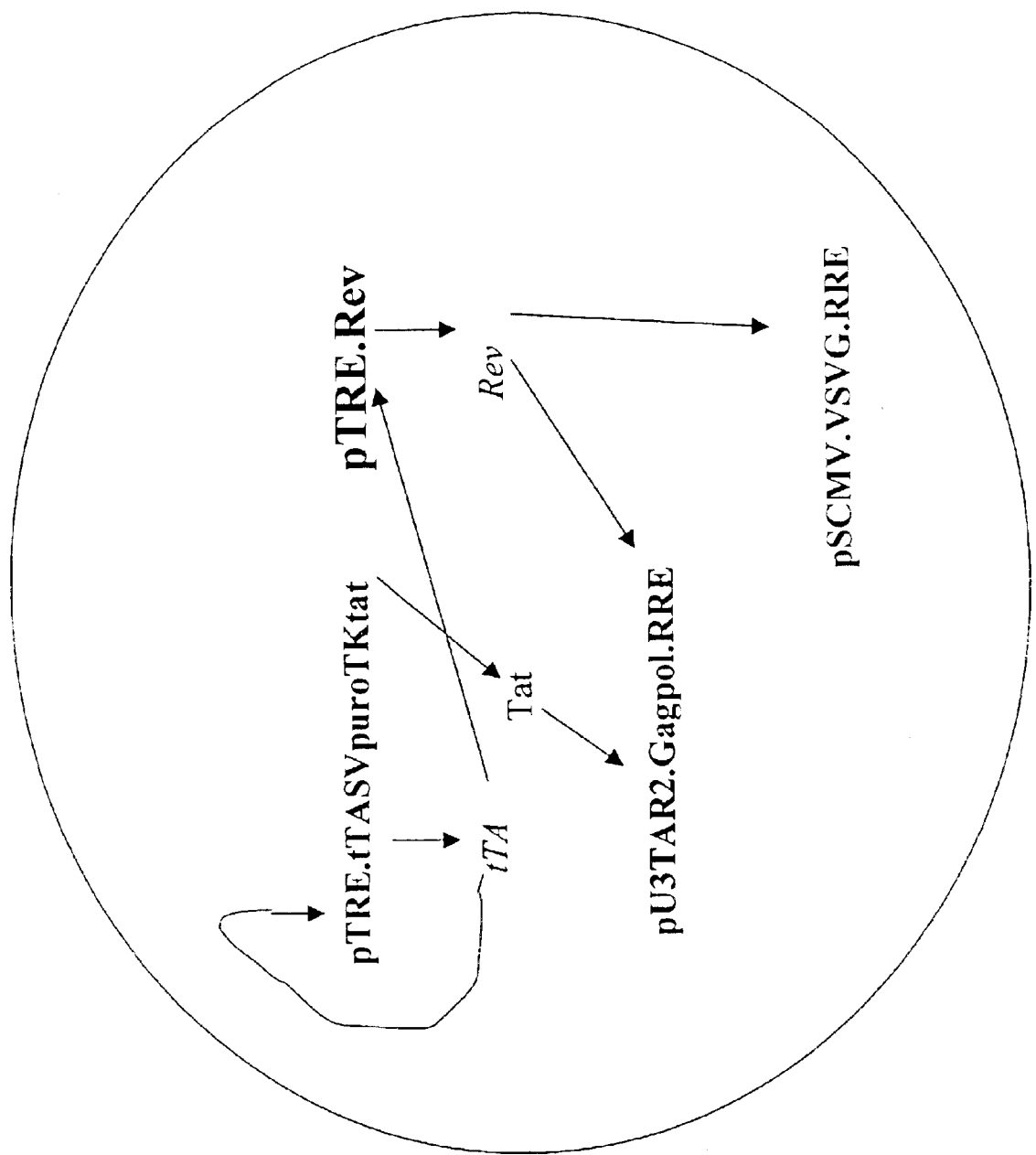
FIG. 1 is a schematic of an expression system of the invention to regulate expression of both a retroviral gag/pol coding region and of VSV-G protein in a cell. The system uses four constructs, with the first being an autoregulated expression construct for tTA under the control of a TRE regulated promoter. The second construct expresses a retroviral rev protein under the control of a TRE regulated promoter. The third construct expresses a retroviral, RRE containing, gag/pol coding region under the control of a chimeric retroviral promoter. The fourth construct expresses an RRE regulated VSV-G transcript under the control of a heterologous promoter, , such as a simian cytomegalovirus promoter.

A "nucleic acid" or "nucleic acid construct" or "nucleic acid molecule" is a polynucleotide or polymeric form of nucleotides of any length, either ribonucleotides or deoxyribonucleotides. This term refers only to the primary structure of the molecule. Thus, this term includes double- and single-stranded DNA and RNA. The term also encompasses linear or circular polymers.

A "coding sequence of interest" as used herein, is a polynucleotide sequence of interest, the expression of which is desired. The coding sequence may be known or not known, in terms of its actual sequence, but encodes an RNA or polypeptide of interest.

As used herein, a "cell" or "host" refers to the corresponding living organism in which the nucleic acid constructs or expression systems of the invention may be introduced and expressed. A "cell" may be any cell, and, preferably, is a eukaryotic cell. The cells may be those of a cell line or primary cells newly isolated and transformed by, or in conjunction with, the introduction of the nucleic acid constructs of the invention. Cell lines or cultures refer to cells maintained via in vitro culturing which may be nonidentical to the parental cell(s) from which the lines or cultures were derived. Non-limiting examples of cells include eukaryotic cell lines, such as HeLa, 293, HT-1080, CV-1, TE671 or other human cells; Vero cells; or D17 cells. Other cells include a lymphocyte (such as T or B cells) or a macrophage (such as a monocytic macrophage), or is a precursor to either of these cells, such as a hematopoietic stem cell. Additional cells for the practice of the invention include an astrocyte, a skin fibroblast, a bowel epithelial cell, an endothelial cell, an epithelial cell, a dendritic cell, Langerhan's cells, a monocyte, a muscle cell, a neuronal cell (such as, but not limited to brain and eye), a hepatocyte, a hematopoietic stem cell, an embryonic stem cell, a cell that give rise to spermatozoa or an oocyte, a stromal cell, a mucosal cell and the like. Preferably, the host cell is of a eukaryotic, multicellular species (e.g., as opposed to a unicellular yeast cell), and, even more preferably, is a mammalian, e.g., human, cell.

A cell can be present as a single entity, or can be part of a larger collection of cells. Such a "larger collection of cells" can comprise, for instance, a cell culture (either mixed or pure), a tissue (e.g., endothelial, epithelial, mucosa or other tissue, including tissues containing the above mentioned CD 4 lacking cells), an organ (e.g., heart, lung, liver, muscle, gallbladder, urinary bladder, gonads, eye, and other organs), an organ system (e.g., circulatory system, respiratory system, gastrointestinal system, urinary system, nervous system, integumentary system or other organ system), or an organism (e.g., a bird, mammal, or the like). Preferably, the organs/tissues/cells are of the circulatory system (e.g., including, but not limited to heart, blood vessels, and blood, including white blood cells and red blood cells), respiratory system (e.g., nose, pharynx, larynx, trachea, bronchi, bronchioles, lungs, and the like), gastrointestinal system (e.g., including mouth, pharynx, esophagus, stomach, intestines, salivary glands, pancreas, liver, gallbladder, and others), urinary system (e.g., such as kidneys, ureters, urinary bladder, urethra, and the like), nervous system (e.g., including, but not limited to, brain and spinal cord, and special sense organs, such as the eye) and integumentary system (e.g., skin, epidermis, and cells of subcutaneous or dermal tissue). Even more preferably, the cells are selected from the group consisting of heart, blood vessel, lung, liver, gallbladder, urinary bladder, and eye cells. The cells need not be normal cells and can be diseased cells. Such diseases cells can be, but are not limited to, tumor cells, infected cells, genetically abnormal cells, or cells in proximity or contact to abnormal tissue such as tumor vascular endothelial cells.

A "portion" or "region," used interchangeably herein, of a polynucleotide or oligonucleotide is a contiguous sequence of 2 or more bases. In other embodiments, a region or portion is at least about any of 3, 5, 10, 15, 20, 25 contiguous nucleotides.

A "virus" is an infectious agent that consists of protein and nucleic acid, and that uses a host cell's genetic machinery to produce viral products specified by the viral nucleic acid. The invention includes aspects, such as expression of viral coding sequences, that may be applied to both RNA and DNA viruses. RNA viruses are a diverse group that infects prokaryotes (e.g., the bacteriophages) as well as many eukaryotes, including mammals and, particularly, humans. Most RNA viruses have single-stranded RNA as their genetic material, although at least one family has double-stranded RNA as the genetic material. The RNA viruses are divided into three main groups: the positive-stranded viruses, the negative-stranded viruses, and the double-stranded RNA viruses. RNA viruses related to the present invention includes Sindbis-like viruses (e.g., Togaviridae, Bromovirus, Cucumovirus, Tobamovirus, Ilarvirus, Tobravirus, and Potexvirus), Picornavirus-like viruses (e.g., Picornaviridae, Caliciviridae, Comovirus, Nepovirus, and Potyvirus), minus-stranded viruses (e.g., Paramyxoviridae, Rhabdoviridae, Orthomyxoviridae, Bunyaviridae, and Arenaviridae), double-stranded viruses (e.g., Reoviridae and Birnaviridae), Flavivirus-like viruses (e.g., Flaviviridae and Pestivirus), Retrovirus-like viruses (e.g., Retroviridae), Coronaviridae, and other viral groups including, but not limited to, Nodaviridae. The invention is applied preferably to an RNA virus of the family Flaviviridae, more preferably a virus of the genus Filovirus, and especially a Marburg or Ebola virus. A virus of the family Flaviviridae is a virus of the genus Flavivirus, such as yellow fever virus, dengue virus, West Nile virus, St. Louis encephalitis virus, Japanese encephalitis virus, Murray Valley encephalitis virus, Rocio virus, tick-borne encephalitis virus, and the like. The invention is preferably applied to a virus of the family Picornaviridae, preferably a hepatitis A virus (HAV), hepatitis B virus (HBV), hepatitis C virus (HBC), or a non-A or non-B hepatitis virus.

Another preferred RNA virus to which the invention may be applied is a virus of the family Retroviridae (i.e., a retrovirus), particularly a virus of the genus or subfamily Oncovirinae, Spumavirinae, Spumavirus, Lentivirinae, and Lentivirus. An RNA virus of the subfamily Oncovirinae is desirably a human T-lymphotropic virus type 1 or 2 (i.e., HTLV-1 or HTLV-2) or bovine leukemia virus (BLV), an avian leukosis-sarcoma virus (e.g., Rous sarcoma virus (RSV), avian myeloblastosis virus (AMV), avian erythroblastosis virus (AEV), and Rous-associated virus (RAV; RAV-0 to RAV-50), a mammalian C-type virus (e.g., Moloney murine leukemia virus (MuLV), Harvey murine sarcoma virus (HaMSV), Abelson murine leukemia virus (A-MuLV), AKR-MuLV, feline leukemia virus (FeLV), simian sarcoma virus, reticuloendotheliosis virus (REV), spleen necrosis virus (SNV)), a B-type virus (e.g., mouse mammary tumor virus (MMTV)), and a D-type virus (e.g., Mason-Pfizer monkey virus (MPMV) and "SAIDS" viruses). An RNA virus of the subfamily Lentivirus is desirably a human immunodeficiency virus type 1 or 2 (i.e., HIV-1 or HIV-2, wherein HIV-1 was formerly called lymphadenopathy associated virus 3 (HTLV-III) and acquired immune deficiency syndrome (AIDS)-related virus (ARV)), or another virus related to HIV-1 or HIV-2 that has been identified and associated with AIDS or AIDS-like disease. The acronym "HIV" or "human immunodeficiency virus" are used herein to refer to these HIV viruses, and HIV-related and -associated viruses, generically. Moreover, an RNA virus of the subfamily Lentivirus preferably is a Visna/maedi virus (e.g., such as infect sheep), a feline immunodeficiency virus (FIV), bovine lentivirus, simian immunodeficiency virus (SIV), an equine infectious anemia virus (EIAV), and a caprine arthritis-encephalitis virus (CAEV). The invention may also be applied to a DNA virus. Preferably, the DNA virus is an herpes virus (such as Epstein-Barr virus, herpes simplex viruses, cytomegalovirus) an adenovirus, an AAV, a papilloma virus, a vaccinia virus, and the like.

It must be noted that as used in this specification and the appended claims, the singular forms "a", "an" and "the" include corresponding plural references unless the context clearly dictates otherwise.

"Expression" includes transcription of a deoxyribonucleic acid and/or translation of a ribonucleic acid.

As used herein, the term "comprising" and its cognates are used in their inclusive sense; that is, equivalent to the term "including" and its corresponding cognates.

Conditions that "allow" an event to occur or conditions that are "suitable" for an event to occur, such as initiation of transcription or translation, strand extension or elongation, and the like, are conditions that do not prevent or inhibit such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as nucleic acid/protein interactions, protein/protein interactions, transcription or translation.

The term "3'" (three prime) generally refers to a region or position in a polynucleotide or oligonucleotide 3' (downstream) from another region or position in the same polynucleotide or oligonucleotide.

The term "5'" (five prime) generally refers to a region or position in a polynucleotide or oligonucleotide 5' (upstream) from another region or position in the same polynucleotide or oligonucleotide.

The term "3'-DNA portion," "3'-DNA region," "3'-RNA portion," and "3'-RNA region," refer to the portion or region of a polynucleotide or oligonucleotide located towards the 3' end of the polynucleotide or oligonucleotide, and may or may not include the 3' most nucleotide(s) or moieties attached to the 3' most nucleotide of the same polynucleotide or oligonucleotide.

The term "5'-DNA portion," "5'-DNA region," "5'-RNA portion," and "5'-RNA region," refer to the portion or region of a polynucleotide or oligonucleotide located towards the 5' end of the polynucleotide or oligonucleotide, and may or may not include the 5' most nucleotide(s) or moieties attached to the 5' most nucleotide of the same polynucleotide or oligonucleotide.

The term "heterologous" refers to a relationship between two materials where they are not normally found together in nature or in their natural state. The term "endogenous" refers to a relationship between two materials where they are normally found together in nature or in their natural state. For example, a coding sequence may be operably linked to a heterologous promoter, which is not normally associated with the sequence in nature, to its endogenous promoter, with which the sequence is normally associated in nature. Alternatively, a nucleic acid may be covalently linked to a heterologous sequence with which said nucleic acid is normally found except that the heterologous sequence is in an antisense orientation. A coding sequence is "operably linked" to a promoter (e.g., when both the coding sequence and the promoter together constitute a native or recombinant construct capable of being expressed) when the promoter is capable of directing transcription of the coding sequence.

Unless defined otherwise all technical and scientific terms used herein have the same meaning as commonly understood to one of ordinary skill in the art to which this invention belongs.

The present invention provides nucleic acid (expression) constructs which, when used in combination, regulate the expression of one or more than one coding sequence of interest. The coding sequence of interest may encode an RNA or polypeptide the expression of which is of interest or desirable. The nucleic acid constructs are preferably recombinant in nature and act sequentially to regulate expression of a coding sequence of interest, which would thus be located on the "last" construct. Each construct results in the expression of a product that regulates expression from the next construct in turn until ultimately, expression of the coding sequence of interest via the last construct is controlled. Each construct preferably, and individually, contains a regulatory region that is inducible and/or regulated by expression from another construct. The constructs optionally also contain selectable or detectable markers to facilitate their identification and use. A regulatory or coding sequence present on a construct but not endogenous to cells in which the construct has been introduced may serve as a detectable marker.

The constructs of the invention are preferably present in a cell or cell line used to package a viral vector. The constructs thus regulate the expression of one or more than one viral component necessary for packaging said vector. The viral component may be any viral gene product that is necessary for proper packaging, including, but not limited to, a viral envelope protein, a capsid protein, the gag or pol encoded proteins in the case of retroviruses, and/or a viral regulatory protein. Nucleic acids encoding these viral components may be placed on one or more than one nucleic acid molecules so long as they may be expressed to result in appropriate packaging of the viral vector. To decrease the likelihood of recombination between the viral vector and the constructs resulting in the vectors containing all viral components, nucleic acids encoding the viral components are preferably divided into separate nucleic acid molecules. Preferred viral components to be expressed are those encoded by the gag/pol sequences of HIV-1 or HIV-2, a retroviral (preferably from HIV-1 or -2) rev protein, and a viral envelop protein.

For example, and without limiting the invention, the invention may comprise three constructs for the expression of a coding sequence of interest. The first nucleic acid construct is capable of expressing a first product, wherein said first product is capable of regulating expression of a second product from a second nucleic acid construct, and wherein said second product is capable of regulating expression of product encoded by said coding sequence of interest, which is present on a third nucleic acid construct. Preferably, at least one of said three nucleic acid constructs comprise heterologous nucleic acids. In other preferred embodiments, expression from the first and second constructs is by direct regulation of transcription and/or translation while expression of the coding sequence of interest from the third construct is by regulation of splicing and/or nuclear export.

In one embodiment of the invention, the first construct comprises an inducible or otherwise regulated promoter, such as the tetracycline promoter/operator or a steroid or ecdysone promoter region. Another regulatory system is that developed by ARIAD Pharmaceuticals Inc. The promoter is operably linked to a first coding sequence encoding a product that regulates expression from the second construct. In one preferred embodiment of the invention, the first construct comprises a tetracycline promoter and a first coding sequence encoding an activator of the tetracycline promoter (or a fusion protein comprising the activator such as, but not limited to, tTA) such that the first construct is autoregulatory and no expression occurs in the presence of tetracycline. Alternatively, the first coding sequence encodes a retroviral, preferably HIV-1 or HIV-2, tat protein.

Induction of transcription by removal of tetracycline in this example results in the expression of tet activator or alternatively, the tat protein. Thus the second nucleic acid construct would comprise a tet promoter/operator or alternatively a tat regulated promoter region, such as a 5' LTR promoter regulated by the expressed tat protein. The coding sequence of said second nucleic acid sequence may encode any product that regulates expression of the third construct. In a non-limiting embodiment of the invention, the second nucleic acid sequence may encode a retroviral rev protein to regulate mRNA splicing and/or nuclear export of the coding sequence of interest present on the third construct. In embodiments of the invention comprising expression of the rev protein, the promoter present on the third construct may be any suitable promoter capable of expressing the coding sequence of interest as mRNA at levels sufficient to result in desirable levels of protein production upon appropriate splicing and/or nuclear export in the presence of the rev protein. Preferably, the promoter is that of a retroviral, preferably HIV, 5' LTR or that of from a cytomegalovirus (CMV), preferably human or simian CMV.

Applied to a packaging cell of the present invention, the coding sequence of interest on the third construct may encode a viral envelope protein (such as that of a retrovirus), more preferably an HIV-1, HIV-2, or MMLV envelope protein; the G protein from Vesicular Stomatitis Virus (VSV), Mokola virus, or rabies virus; GaLV, Alphavirus E1/2 glycoprotein, or RD114, an env protein from feline endogenous virus. Alternatively, sequences encoding a chimeric envelope protein may also be used. Sequences encoding an envelope protein from the following viral families may also be used: Piconaviridae, Tongaviridae, Coronaviridae, Rhabdoviridae, paramyxoviridar, Orthomixoviridae, Bunyaviridae, Arenaviridae, Paroviridae, Poxviridae, hepadnaviridae, and herpes viruses.

In an alternative embodiment of the invention, and where the first construct comprises a tetracycline promoter/operator operably linked to a coding sequence for a steroid hormone receptor, the induction of expression results in expression of said receptor. The second construct would thus have a promoter that is regulated by said steroid hormone receptor (initiation from said promoter is activated by a complex comprising the receptor and an activating ligand). In the absence of said complex, the promoter is inactive. The coding region of the second construct may again encode any product which regulates expression from the third construct. For example, the coding sequence of the second construct may encode a retroviral tat or rev protein. With an encoded tat protein, the third construct comprises a region which permits expression to be regulated by the tat protein, such as, but not limited to, a retroviral 5' LTR promoter and sequences encoding a cis-acting RNA element, designated the TAR. With an encoded rev protein, expression of the third construct only needs to be under the regulation of the rev protein (via mRNA splicing and/or nuclear export control) as discussed above.

Applied to cells for packaging a viral vector, the retroviral tat protein may be from a heterologous virus relative to that of the viral vector. The viral vector may be HIV-1 derived, and without limiting the invention, a chimeric retroviral promoter may be used in one or more of the nucleic acid constructs of the invention. A non-limiting example of a chimeric retroviral promoter is a retroviral 5' LTR promoter containing a heterologous TAR sequence such that expression of the cognate heterologous tat protein is needed for expression of the coding sequence linked to the promoter. A preferred chimeric promoter comprises an HIV-1 5' LTR promoter containing a HIV-2 TAR sequence. When used in combination with a construct capable of expressing an HIV-2 tat protein, the coding sequence operably linked to the chimeric promoter is expressed.

In additional embodiments of the invention wherein a TAR element is used in one or more than one construct of the invention, a tat protein coding sequence need not be present in any construct of an expression system as disclosed herein. Instead, the requirement of the TAR for a cognate tat protein may be met by supplying tat protein from another source. For example, and wherein the constructs of the invention are introduced into a cell, the cell may contain an additional nucleic acid construct, optionally integrated into the cellular genome, that expresses the necessary tat protein. Such simple expression constructs are well known in the art.

One example of the above is where a tat protein is used in combination with an expression system of the invention. Where two nucleic acid sequences of interest are to be expressed, the first can be under the control of an expression system of the invention while the second is under the control of both said system and a tat protein expressed via another source as described above. For example, three constructs may be used to regulate expression of the first sequence of interest (from the third construct) via a rev protein (from the second construct). The second sequence of interest is then expressed from a fourth construct that is regulated by the rev protein (from the second construct) and the tat protein. Thus the first sequence of interest is only under the control of the system while the second sequence of interest is under the control of both the system and a tat protein. Heterologous tat proteins and TAR elements may of course be used in this alternate embodiment of the invention. In a further alternative, the first sequence of interest may also be made to be tat regulated.

As an alternative to the use of tat coding sequences described above, sequences encoding a chimeric tat protein may be used. Tat has be made into a fusion protein (e.g. Tat-Gal4) and shown to retain its transactivating activity of the HIV-LTR promoter. Other chimeric Tat proteins may also be used so long as sufficient transactivating activity is retained.

Whenever rev protein is used to regulate the expression from a subsequent construct, the coding sequence of said subsequent construct contains, or is modified to contain, a rev responsive element (RRE) and appropriate splice donor and acceptor sites for regulation by rev protein. For example, and without limiting the invention, where the third construct comprises a coding sequence encoding a viral envelope or G protein, the coding sequence comprises splice donor and acceptor sites that require a cognate rev protein for appropriate splicing and/or nuclear export so that the envelope or G protein may be expressed. The sites may optionally be selected to provide attenuated splicing function in conjunction with the rev protein. Attenuation provides a means to make expression more dependent on the rev protein and the RRE. For example, if the splice sites intrinsically function too quickly, the coding sequence of interest may be spliced out before the rev protein and RRE have an opportunity to export the mRNA and permit expression of the sequence. The splice sites are thus selected to be sufficient to permit splicing and suppress expression in the absence of rev protein while suppressing splicing and permitting expression in the presence of rev protein.

The constructs of the invention may be viewed and used in combination as an expression system for the coding sequence of interest. Moreover, two or more expression systems comprising identical constructs may be combined to regulate expression of two or more coding sequences of interest simultaneously. For example, and without limiting the invention, the first two constructs may be identical with the second construct regulating the expression of coding sequences of interest on two or more third constructs, each capable of expressing a coding sequence of interest. In one embodiment of this example, the first construct may comprise a tetracycline inducible promoter operably linked to a coding sequence encoding a product which regulates expression of a rev protein coding sequence in the second construct. The coding sequences of interest in each of the two or more third constructs are modified to contain splice donor and acceptor sites so that expression of the encoding proteins occurs upon the presence of rev protein expressed by the second construct. In a specific example, two coding sequences of interest may be present in two third constructs: the first coding sequence is a retroviral, preferably HIV, gag/pol sequence operably linked to an RRE, and the second coding sequence is a VSV-G or Mokola virus G protein operably linked to an RRE. As noted above, the promoters for these two third constructs may be any promoter capable of sufficient expression upon the presence of the rev protein.

As noted herein, expression from the first nucleic acid construct is preferably tightly regulated or even autoregulated. As a non-limiting example, tight regulation is provided a positive feedback mechanism where the product of the first nucleic acid construct can repress (directly or indirectly) its own expression. In the absence of activation, this autoregulation of the first nucleic acid construct results in very low basal activity such that little to no expression from the other constructs of an expression system of the invention occurs. Instead, and upon activation of expression from the first nucleic acid construct, the expression of all additional constructs in the system follows.

The constructs and systems of the invention may be incorporated into vectors or introduced into cells, such as, but not limited to, mammalian, rodent, primate, or human cells. The constructs of the invention may be integrated into the cellular genome or maintained as episomal constructs. Preferred cells of the invention are those in which expression of a coding sequence of interest, alone or in combination with other nucleic acid expression is desired. The constructs of the invention may be introduced into cells in any order. After introduction, the presence of the constructs in said cells may be confirmed by detecting said constructs via a selectable or detectable marker placed on said construct.

While each construct of the invention may be present on an individual nucleic acid molecule, some preferred applications of the invention include a single nucleic acid molecule containing more than one construct of the invention. For example, and as a non-limiting example relating to the preparation of a stable cell line, the constructs of the invention are stably integrated into one or more than one chromosome of a cell to produce a stably transfected cell line. Alternatively, the constructs may be placed on one or more than one episomal vector or plasmid before introduction into said cell. Applied to cells for the packaging of viral vectors, the individual constructs are preferably divided into separate nucleic acid molecules to increase the number of recombinations with the viral vector required to render it replication competent. Preferably, the constructs of the invention, especially the regulatory and coding sequence portions thereof, comprise sequences that are viral in origin. Thus viral regulatory regions (which act in cis) and coding regions (which act in trans) are preferred for the practice of the invention. Examples of cis acting regions are the TAR and RRE, INS (inhibitory sequence or instability sequence, also referred to as CRS) elements of retroviruses, while examples of trans acting coding regions are the tat and rev coding sequences. Cells used with viral constructs are preferably free of viral sequences other than those to be introduced by the constructs of the invention.

Preferably, an RRE heterologous to the viral nucleic acid of interest is used in the constructs of the invention. Examples include, but are not limited to, HIV-2 RRE for an HIV-1 derived nucleic acid, a CTE (constitutive transport element such as that from Mason-Pfizer monkey virus and other retroviruses) or a PRE (post-transcriptional regulatory element such as that from the woodchuck hepatitis virus. In addition to diminishing, minimizing or eliminating the possibility of homologous recombination based on the different RREs having different sequences, a surprising and unexpected increase in the production of packaged viral nucleic acid of as much as approximately five-fold has been observed.

Among the various embodiments of the invention is the expression of coding sequences of interest wherein the encoded product is toxic to the cell or host in which expression occurs. Examples of this include viral gag-pol proteins and envelope proteins such as the VSV G protein. The full scope of the invention, however, includes its use to express sequences that are either not toxic to a cell or host or toxic only under specific conditions, such as expression at high levels or in the presence of additional factors that contribute toxicity.

One preferred aspect of the invention relates to the preparation of cells and cell lines containing the constructs of the invention. Methods for the introduction of nucleic acid constructs into cells, including the use of conditions conducive to integration into the cellular genome (such as electroporation, lipofection, and calcium phosphate precipitation), are known in the art. In preferred embodiments, the constructs and cells are designed to provide the necessary factors to produce viral particles containing a particular viral nucleic acid of interest. Preferably, the viral nucleic acid is replication deficient and derived from a naturally occurring virus without removal or loss of the endogenous "packaging signal". In particularly preferred embodiments of the invention, the viral nucleic acid is derived from HIV-1. HIV-1 derived viral nucleic acids may be produced by the pNL4-3 HIV-1 molecular clone which is a wild-type strain which is available from the AIDS Research and Reference Reagent Program Catalog through the National Institutes of Health (see, also, Adachi et al., J. Virol., 59, 284–291 (1986)). These cells may be viewed and used as "packaging cells" for the viral nucleic acid, which may be separately introduced into the cell, because they produce all the components necessary to package the viral nucleic acid into infectious viral particles.

Preferred packaging cells express from a coding sequence of interest at least a viral envelope protein, or equivalent (such as a mutant, fusion, or truncated form thereof) or heterologous form thereof, when the viral nucleic acid provides all other components. Preferred envelope proteins are those encoded by sequences endogenous to the viral nucleic acid in its natural form (i.e. that is normally used in the packaging of the virus from which the viral nucleic acid is derived) or heterologous to the viral nucleic acid. A variety of envelope proteins may be expressed in the practice of this aspect of the invention, including proteins to alter the target cell specificity of a packaged viral particle or alternate envelope proteins that result in pseudotyped viral particles. Preferred heterologous envelope proteins for use with HIV-1 derived viral nucleic acids include the VSV G protein, the Mokola virus G protein, and the HIV-2 envelope protein.

Alternatively, the cells provide at least a viral envelope protein and one or more than one protein necessary for expression of packaging components from the viral nucleic acid to be packaged. A non-limiting example are cells which provide both an envelope protein as well as a cognate tat protein, or one or more than one other protein required in trans, to package a retroviral nucleic acid (e.g. cells that provide a VSV G protein and an HIV-1 tat protein to package an HIV-1 derived vector). Examples of additional proteins required in trans include those encoded by gag, pol, and rev sequences.

Preferably, the viral nucleic acid of interest to be packaged lacks the ability to express or encode one or more than one viral accessory protein sequences (such as, but not limited to, Vif, Vpu, Vpr or Nef, or combinations or fragments thereof) that would make the nucleic acid pathogenic or possibly pathogenic. This may be achieved by removal of the corresponding coding sequences or mutating them to prevent their expression at the transcription or translation level. Such proteins, to the extent that they are necessary for packaging, would be supplied by the packaging cell either via the constructs of the invention or by an additional nucleic acid construct.

Expression of one or more than one viral protein by a packaging cell of the invention may be confirmed by a variety of methods known in the art, including an ELISA method such as a sandwich ELISA using one or more than one antibody to recognize the viral protein(s). Other non-limiting examples of methods include immunostaining and Western blotting.

Viral nucleic acids of interest to be packaged by such cells may optionally contain one or more than one heterologous sequence of interest for packaging by the aforementioned packaging cells. Examples of such heterologous sequences include a genetic antiviral agent as described in U.S. Pat. No. 6,168,953. Exemplars include ribozymes, antisense sequences, and/or nucleic acid decoys.

In one preferred embodiment of the invention, the viral nucleic acid is a conditionally replicating vector as described in U.S. Pat. No. 5,885,806 and co-pending U.S. patent application Ser. No. 09/562,894 filed May 1, 2000. In another preferred embodiment, the viral nucleic acid is such a conditionally replication vector that also includes endogenous sequences encoding the gag and pol proteins. The cells may thus be viewed and used as a system for packaging said heterologous sequence(s) into viral particles. The particles may then be viewed and used as a delivery vehicle for the packaged sequence(s) to cells by infection.

In yet another preferred embodiment, the viral nucleic acid and the constructs of the invention are designed so that there is a minimum of identity between their sequences to reduce the possibility of recombination between them to reduce the likelihood of generating replication proficient viral nucleic acids. Preferably, there is fewer than about 8 identical nucleic acid residues between a viral nucleic acid and the constructs of the invention, although fewer than about 6 and about 4 identical residues is even more preferred. Methods to introduce such non-identity include removing non-expressed or non-critical sequences from the viral nucleic acid and/or the constructs or degenerating sequences that are found in both to reduce the frequency of sequential identical residues.

Methods for the use of the constructs of the invention include their introduction into cells capable of expressing them to produce a cellular expression system for one or more coding sequence of interest. Such cellular systems may optionally be introduced into a multicellular host or already present in such a host to express a coding sequence of interest in vivo. The cellular expression system may be used to express said coding sequence of interest either for subsequent isolation or purification or to be used in other cellular metabolic activity such as the packaging of viral particles.

The packaged viral particles may be found in the supernatant surrounding the packaging cells and optionally isolated therefrom. The particles will preferably have both a high titer and transduction efficiency to introduce the packaged viral nucleic acid of interest into a target cell.

In another aspect of the invention, the invention provides methods for the production of the disclosed constructs and systems by methods known in the art. The recombinant use of various nucleic acid constructs, including nucleic acid splicing and cell transformation techniques are well established in the art and may be used without unnecessary experimentation. Regarding cells for the packaging of viral vectors, the invention provides methods for the culturing of such cells after introduction of said viral vector under conditions conducive to cell growth and vector production by methods well established in the art.

In a further aspect of the invention, the constructs and systems thereof may be prepared in the form of a kit for use in the expression of one or more than one sequence of interest. Such a kit optionally includes other components necessary for the practice of the invention, including, but not limited to, appropriate cell lines, buffers, salts, lyophilization stabilizers, or stabilization aids. Kits of the invention comprise the constructs as described herein and may also include other materials that facilitate the practice of the invention, such as, but not limited to, devices for the use of the invention and/or use of the constructs, systems, or cells comprising them. The items comprising the kit may be supplied in the form of individual packages and/or packaged together, as desired by the skilled practitioner.

In one embodiment, a kit comprises at least one expression system in a suitable container. Preferably, the kit contains at least an indication, such as, but not limited to, packaging or a label, identifying the kit, the items as suitable for use in the applications described herein for the present invention and/or at least one instruction relating to the use of the kit or the items in the applications described herein for the present invention. Optionally, the at least one instruction may be part of a larger set of instructions relating to the use of the kit or the item in the applications described herein for the present invention or relating to the use of the kit or the compound in the practice of the present invention. Even more preferred are such kits indicated as suitable for use in expressing a sequence of interest and by way of the packaging, label, or instructions.

EXAMPLES

The present inventive compounds and methods are further described in the context of the following examples. These examples serve to illustrate further the present invention and are not intended to limit the scope of the invention.

Example 1

Regulation by the Tetracycline Gene Regulation System

FIG. 1 shows a schematic of an exemplary regulated gene expression system of the invention where two coding sequences of interest, a retroviral gag/pol sequence and a VSV-G envelop protein, are simultaneously regulated by expression from two other nucleic acid constructs. The system may thus be viewed as a combination of two systems of three nucleic constructs each where the first and second constructs are commonly used between the two systems.

In a preferred expression system of the invention, tTA is expressed from the TRE promoter (tet operon) to permit both high inducible expression levels and low basal expression in the absence of induction. This follows because the TRE promoter is very weak and any tTA expression from the promoter will be fully inactivated by the presence of tetracycline in contact with the system. Upon removal of tetracycline, tTA expression is strongly induced by a positive feedback mechanism to produce high levels of tTA which induces expression of the second nucleic acid construct.

Figure 2:
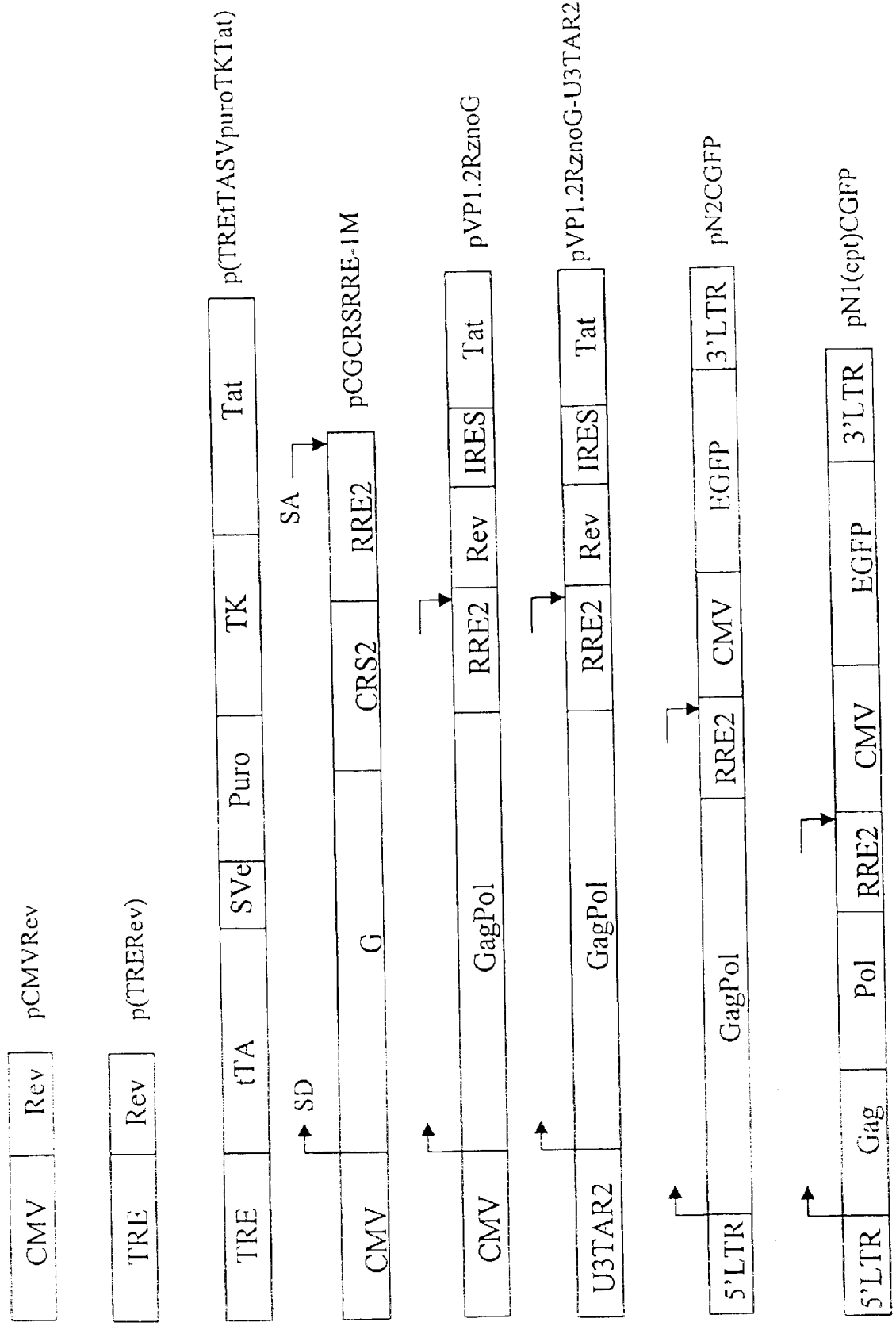
FIG. 2 shows the structures of a number of different nucleic acid constructs of the invention. Constructs that place the rev coding sequence under control of a cytomegalovirus (CMV) or tetracycline (TRE) promoter are shown. The organization of pTRE-tTASvPuroTKTat is described in Example 1 herein. pCGCRSRRE-1M is detailed in part in FIG. 5. Plasmids pVP1.2RznoG and pVP1.2RznoG-U31TAR2 (where IRES is an internal ribosome entry site) are detailed in Example 4 herein. Plasmids pN2CGFP and pN1(cpt)CGFP are discussed in Examples 3 and 4 herein.

Schematic diagrams of the structures of the first two constructs, pTRE-tTASvPuroTKTat and pTRE-Rev (FIG. 1) are shown in FIG. 2. In pTRE-tTASvPuroTKTat, tTA is expressed from TRE promoter, Tat is expressed from the HSV TK promoter, and the selection marker puromycin resistant gene is expressed from SV40 early promoter. Where integration of both constructs into cells have occurred, Rev expression in the cells would be under the control of tetracycline as described above.

Example 2

Construction of HT1080 Based Packaging Cell Lines

HT1080 cells were cotransfected with pTRE.Rev and pTRE.tTASvPuroTKTat plasmid DNA at a molar ratio of 10:1. The transfected cells were cultured in media that selected for puromycin resistance. After 2 to 3 weeks single cell colonies formed and were selected and expanded and screened by immunostaining using an anti-Rev antibody.

Figure 3:
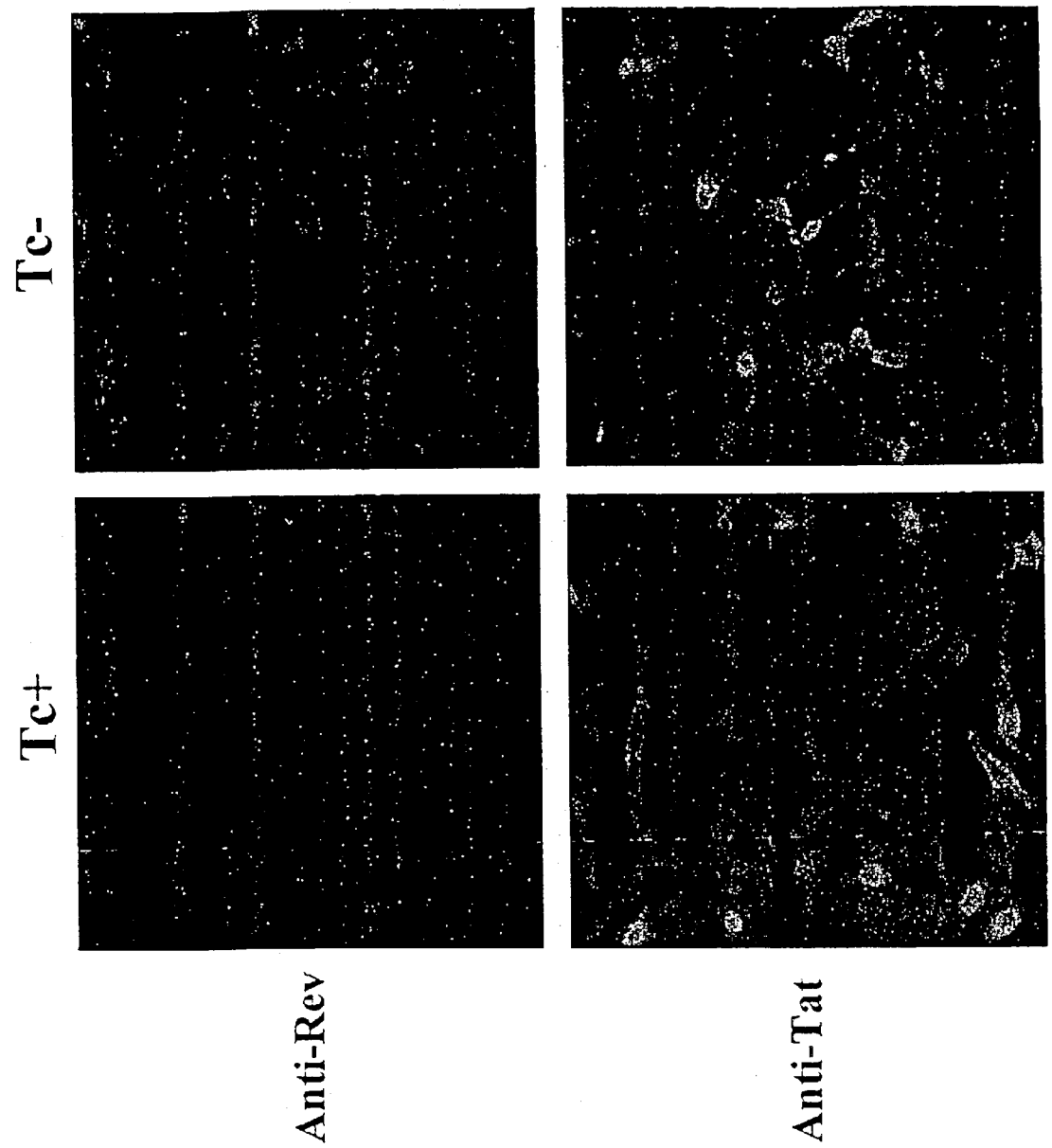
FIG. 3 shows a transfected HT1080-TR clone immunostained with anti-Rev and anti-Tat antibodies in the presence or absence of tetracycline to regulate rev expression. See Example 2 herein.

Regulation of Rev expression by tetracycline: cells from one of the positive clones, 2A3(1)-2-F7, were grown in a 4-well chamber slide in the presence or absence of tetracycline for 48 hours. Cells were then fixed and stained with anti-Rev antibody or anti-Tat antibody. FIG. 3 shows that Rev expressed from TRE promoter is tightly controlled by tetracycline. There was no positive cell in the presence of tetracycline, however, almost every single cell was stained positively using anti-Rev antibody in the absence of tetracycline. Because the Tat gene was constitutively expressed from the HSV TK promoter, almost all the cells were stained positively by anti-Tat antibody both in the presence and absence of tetracycline. These results indicate that the Rev expression is tightly regulated by tetracycline and tTA that is expressed from the TRE promoter.

Example 3

Viral Vector Packaging

Selected HT1080-TR clones were further purified by limited dilution in 96-well plates. Five final clones were selected based on immunostaining and were further analyzed for vector production by cotransfection. HT1080-TR clones that are >90% purity were plated in 6-well plates at a cell density of $1 \times 10^6$ cells/dish and transfected with 5 mg each of pN2CGFP and pCGCRSRRE 24 hours after removal of tetracycline (Tc) and adding 2.5 mM sodium butyrate. pN2CGFP is an HIV-1 based replication deficient viral vector that contains a gag-pol gene expressed from the 5'-LTR, an RRE following the gag-pol gene, and a green fluorescent protein (GFP) gene expressed from an internal CMV promoter. The general structure of pCGCRSRRE is shown in FIG. 2, where "G" refers to the VSV-G protein.

Post transfection, the medium was changed to 3 ml of Tc-free and sodium butyrate-free media for 48 hours before collection of supernatants for use in transducing HT1080 cells. 48 hours post transduction, the transduced cells were analyzed for GFP expression by FACS. Vector titer was determined by % of GFP expression cells. The results are shown in the following Table 1, where clones 2A(1)-2-E5 and 2A3(2) produced relatively high titers among the five final clones.

TABLE 1

| Sample | Clone | Vector Production Titer(IU/ml) | |
|---|---|---|---|
| No | name | Tc+ | Tc− |
| 1 | HT1080 | 2 × 10e2 | |
| 2 | " | | |
| 3 | " | | 6.0 × 10e2 |
| 4 | " | | |
| 5 | 2A2(1)-2-E5 | 4.5 × 10e3 | |
| 6 | " | | |
| 7 | " | | 4.8 × 10e4 |
| 8 | " | | |
| 9 | 2A3(1)-2-F7 | 7.3 × 10e3 | |
| 10 | " | | |
| 11 | " | | 1.5 × 10e4 |
| 12 | " | | |
| 13 | 2A3(2) | 5.8 × 10e3 | |
| 14 | " | | |
| 15 | " | | 6.3 × 10e4 |
| 16 | " | | |
| 17 | 7A2(2) | 6.3 × 10e3 | |
| 18 | " | | |
| 19 | " | | 1.7 × 10e4 |
| 20 | | | |
| 21 | HT1080-P | | 1.6 × 10e4 |
| 22 | " | | |

All samples were conducted in duplicate. The HT1080 controls were co-transfected with all four plasmids simultaneously to result in transient transfection of the plasmids in the cells. End-point titer of the four HT1080-TR clones are in the following order: 2A3(2)>2A2(1)-2-E5>7A2(2) >2A3(1)-2-F7. As evident from the Table, vector production by use of the HT 1080-TR clones is higher than that of a transient transfection system like that of the HT1080 control. Clones 2A(1)-2-E5 and 2A3(2) have 10 fold induction in medium containing no tetracycline. These two clones were selected for further use.

Example 4

Regulation of Genes of Interest by Tat and Rev Expression

Figure 4:
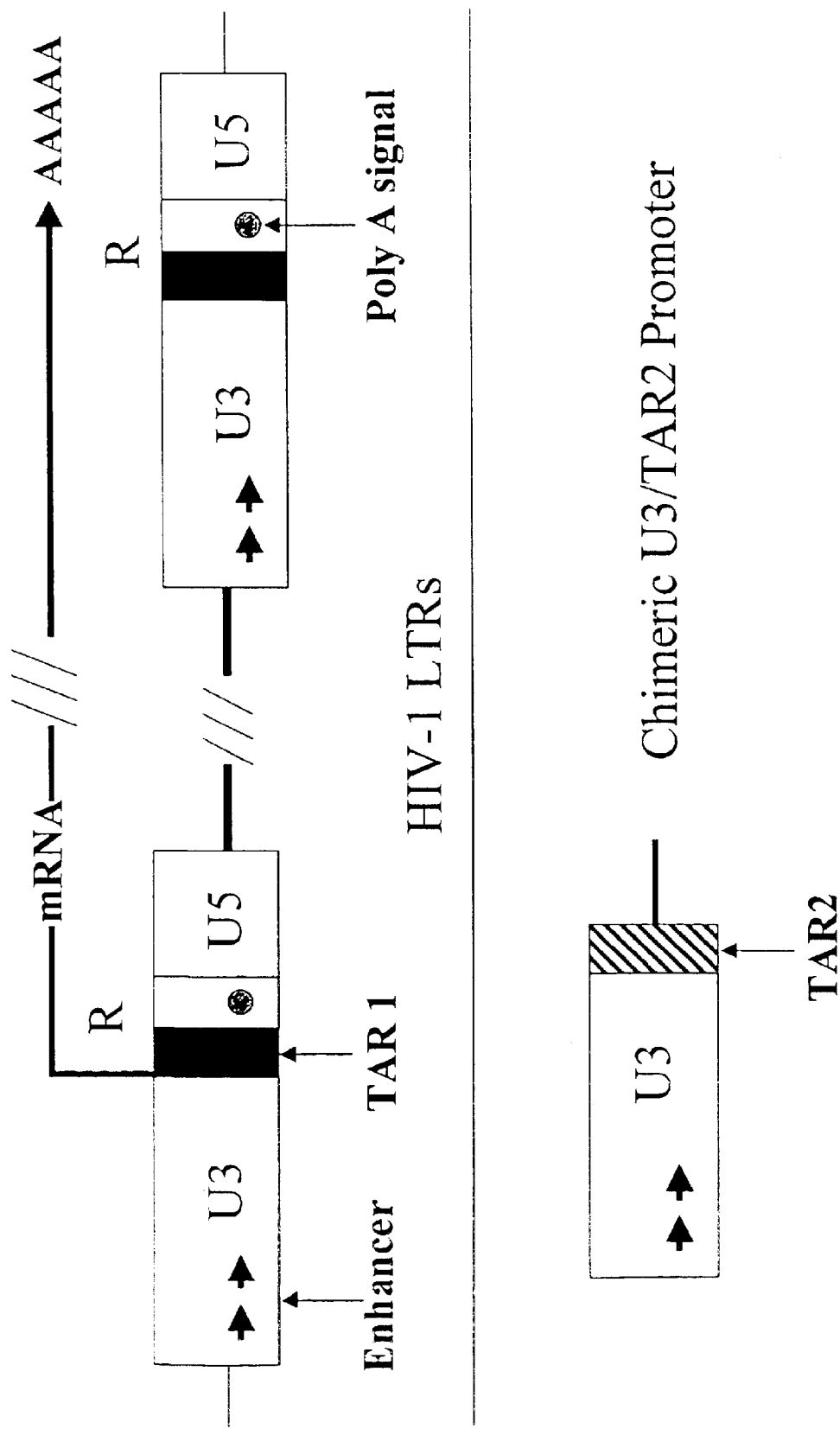
FIG. 4 shows schematics of the chimeric U3/TAR2 promoter discussed in Example 4 herein.

We have previously demonstrated that a HIV-1 gag-pol gene (expressed from a CMV promoter) followed by a downstream HIV-2 RRE (RRE2) can be regulated by HIV-1 Rev. Chang et. al (Nucl. Acids Res. 20(20):5465–5472, 1992) found that the chimeric HIV-1 LTR with the authentic TAR (TAR1) element replaced by HIV-2 TAR (TAR2) can be activated by HIV-1 Tat. Since only the TAR element was replaced the rest of R and U5 in the HIV-1 LTR is still present in this chimeric LTR. The present invention includes a chimeric promoter U3/TAR2 that contains only the HIV-1 U3 and TAR2 (FIG. 4) which was used to replace the CMV promoter that expresses gag-pol in construct pVP1.2RznoG (see FIG. 2) to make pVP1.2RznoG-U31TAR2 (see FIG. 2). Plasmid pVP1.2RznoG or pVP1.2RznoG-U31TAR2 was cotransfected with pN1CGFP and pCGCRSRRE into 293T cells. Supernatant was collected 48 hours after transfection and was titered on HT1080. Both constructs were found to produce equal amount of packaged vectors (pN1CGFP). The titers were $9.0 \times 10^6$ and $9.2 \times 10^6$ TU/ml for pVP1.2RznoG and pVP1.2RznoG-U31TAR2, respectively (where TU represents transforming units). This result indicates the chimeric promoter can be transactivated by Tat to express at a level comparable to that of the CMV promoter.

Example 5

Regulation of Genes of Interest by Rev Expression

Hammarskjold et al. (J. Vir. 68(2):951–958, 1994) found that expression of the HIV-1 env gene (containing the RRE element) is regulated by Rev only when it is in an intron. If the env gene is expressed as a non-intron cDNA, the env gene expression is no longer regulated by Rev. Chang and Sharp (Cell 59:789–795, 1989) found that gene expression regulated by Rev is dependent on the strength of the splice donor signal. If the splice donor signal is very strong and the RNA is very efficiently spliced, gene expression could not be regulated by Rev.

A series of VSV-G expression constructs were made in which the VSV-G cDNA ("gene") was inserted in an intron. Downstream of the VSV-G coding region ("gene") are the CRS element and the RRE. The 3' end of RRE contains a splice acceptor site (see "Rev-responsive" in FIG. 5). Five different splice donor (SD) signals were cloned in front of the VSV-G cDNA (see Table 2 below).

TABLE 2

| Consensus SD | NAGGTAAGT |
| --- | --- |
| Beta-globin SD | CAGGTAAGT |
| HIV-1 major SD | CTGGTGAGT |
| HIV-1 env SD | GCAGTAAGT |
| HIV-2 env SD | CAAGTGAGT |
| Hammarskjold's SD | AGGGTGAGT |

Figure 5:
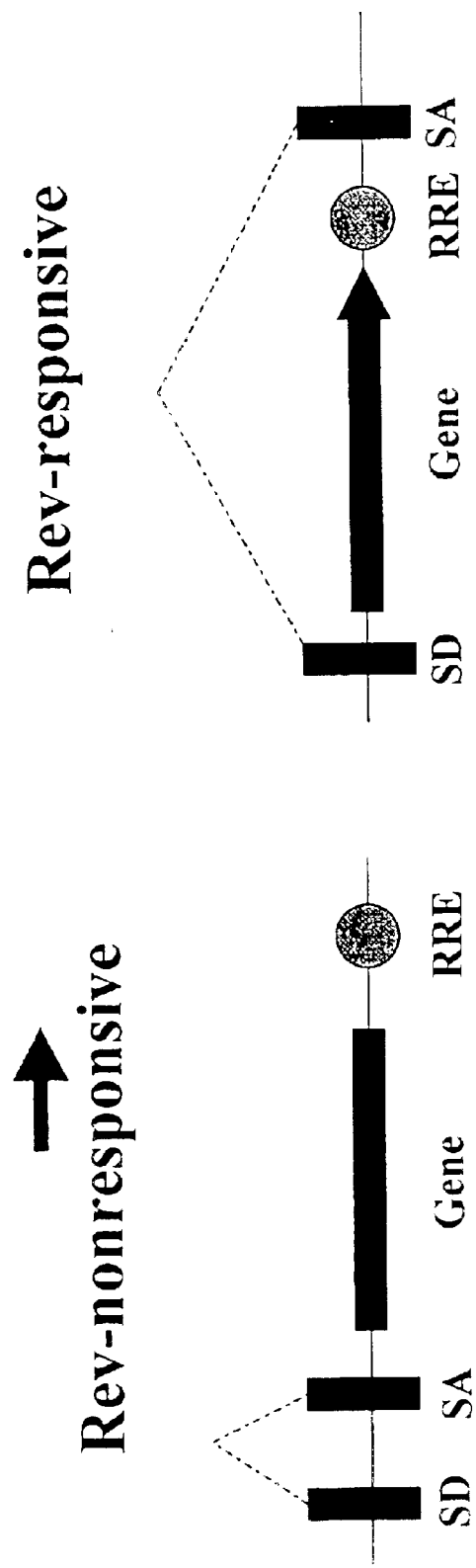
FIG. 5 shows schematics of constructs containing different arrangements of splice donor and acceptor sites to render gene expression Rev responsive (dependent) or non-responsive (independent).
Figure 6:
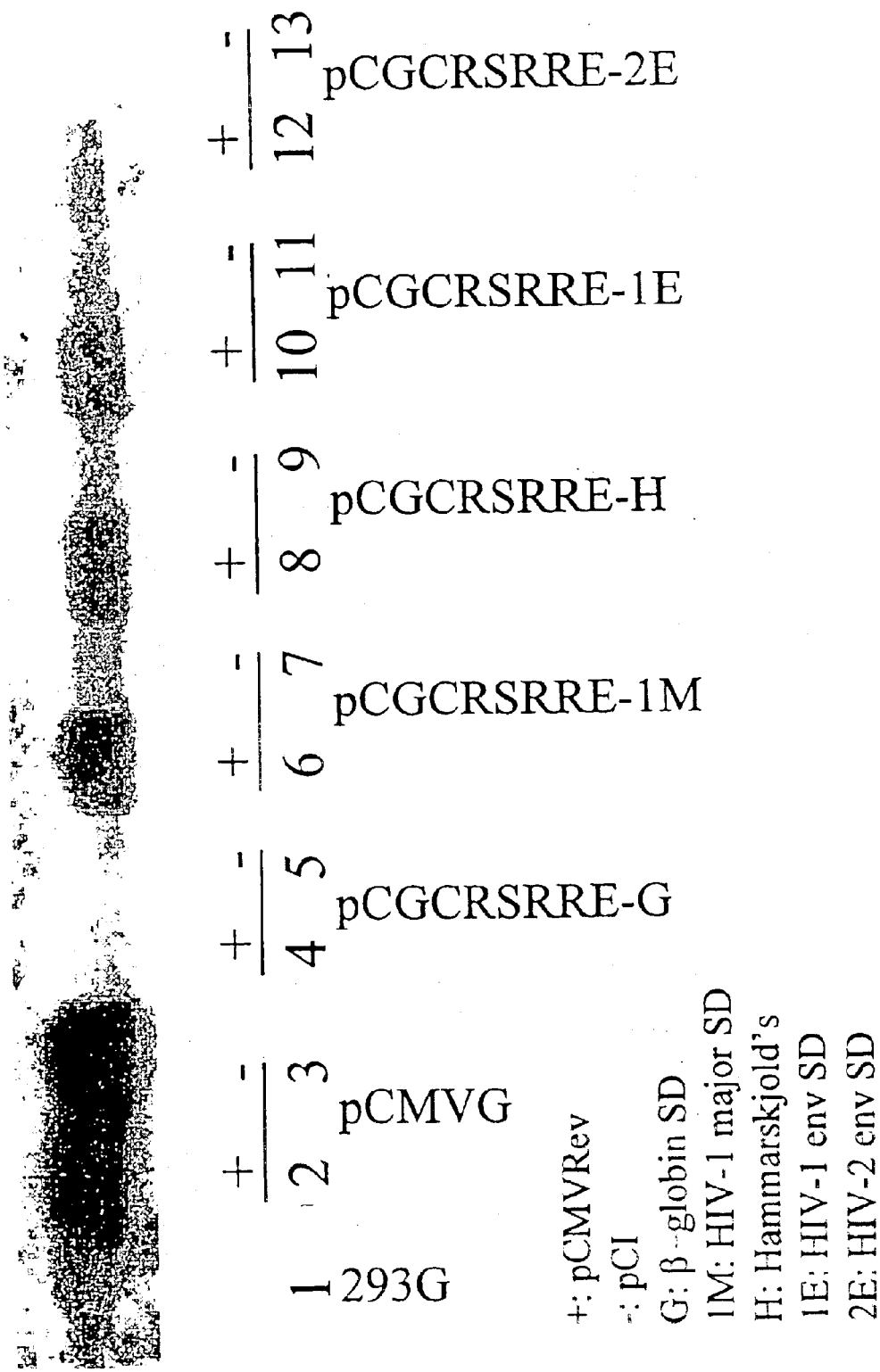
FIG. 6 shows a western blot demonstrating rev-dependent VSV-G protein expression via the use of different splice donor sites.

The entire VSV-G, CRS, and RRE regions are thus expressed as an intron (see FIG. 5, "Rev-responsive"). These five VSV-G expression construct were tested in 293T cells to see whether the expression of VSV-G is regulated by Rev. The result is shown in FIG. 6. These five constructs were co-transfected with either pCMVRev (a rev expression construct ) or pCI (a parental construct of pCMVRev which does not contain the Rev gene, and used as a negative control) into 293T cells. A western blot (Fog/6) shows that VSV-G expression is regulated by Rev in those cells transfected by three of the five constructs.

VSV-G protein is detected in cells co-transfected with pCMVRev and any one of pCGCRSRRE-1M or pCGCRSRRE-H or pCGCRSRRE-1E. However, VSV-G is not detected in cells co-transfected with pCI and any one of pCGCRSRRE-1M or pCGCRSRRE-H or pCGCRSRRE-1E. The data show that the VSV-G expression from these three constructs is regulated by Rev.

There was no VSV-G detected in those cells that were transfected with the other two constructs (pCGCRSRRE-G and pCGCRSRRE-2E). The beta-globin splice donor signal in pCGCRSRRE-G is identical to the consensus splice donor signal and the HIV-2 env splice donor signal in pCGCRSRRE-2E is one nucleotide different from the consensus sequence (see above). It is likely that these splice donor signals are too strong (splice too efficiently) to permit regulation by Rev.

It should be noted that VSV-G is expressed in the cells transfected with pCMVG, the expression is independent of rev expression. There are no CRS, RRE, and splice signals in this construct, which directly expresses VSV G protein under the control of the CMV promoter.

The above demonstrate the identification of three VSV-G expression constructs where expression of VSV-G from the constructs can be regulated by Rev.

All references cited herein, including patents, patent applications, and publications, are hereby incorporated by reference in their entireties, whether previously specifically incorporated or not, for all purposes. Citation of any reference herein is not intended as an admission that any of the foregoing is pertinent prior art, nor does it constitute any admission as to the contents or date of these documents.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A packaging cell comprising:
   a first nucleic acid construct comprising a nucleotide sequence encoding a first inducible promoter and a first product, wherein the first inducible promoter regulates expression of first product and the first inducible promoter is selected from the group consisting of a tetracycline promoter/operator, a retroviral long terminal repeat (LTR) and a steroid promoter region;
   a second nucleic acid construct comprising a nucleotide sequence encoding a second inducible promoter and a second product, wherein the second inducible promoter is induced by the first product and the second product encodes a viral RNA binding protein; and
   a third nucleic acid construct comprising a nucleotide sequence encoding a third inducible promoter and a viral gene product, wherein the third inducible promoter is induced by the second product.

2. The cell of claim 1 wherein said first product is a transactivator of a tetracycline promoter/operator or a fusion protein comprising said transactivator.

3. The cell of claim 1 wherein said second inducible promoter is a tetracycline promoter/operator.

4. The cell of claim 1 wherein said viral RNA binding protein is a rev protein.

5. The cell of claim 1 wherein said third inducible promoter is derived from a retroviral 5' LTR.

6. The cell of claim 1 wherein said first product is a tat protein or a chimeric protein comprising a tat protein.

7. The cell of claim 1 which is stably transfected with said nucleic acid constructs.

8. The cell of claim 1 further comprising a conditionally replicating viral vector and wherein said cell packages said vector.

9. The cell of claim 8 wherein said vector is derived from HIV-1.

10. The cell of claim 9 wherein said viral gene product is a VSV or Mokola virus G protein.

11. The cell of claim 1 wherein the viral gene product is a viral envelope protein or a G protein.

12. The cell of claim 11 further comprising an additional nucleic acid construct that encodes retroviral gag and pol proteins.

13. The cell of claim 11 wherein said viral gene product is a G protein.

14. The cell of claim 11 wherein said viral RNA binding protein is a rev protein.

15. The cell of claim 11 further comprising a conditionally replicating viral vector and wherein said cell packages said vector.

16. The cell of claim 15, wherein said vector is derived from HIV-1.

17. A method of packaging a viral vector comprising culturing the cell of claim 16 under conditions wherein said first nucleic acid construct expresses said first product.

18. The cell of claim 1, wherein said second product encodes rev and said third construct further comprises a nucleotide sequence encoding a rev responsive element (RRE).

19. A method of packaging a viral vector comprising culturing the cell of claim 9 under conditions wherein said first nucleic acid construct expresses said first product.

* * * * *